(12) United States Patent
Biesel et al.

(10) Patent No.: US 8,523,799 B2
(45) Date of Patent: Sep. 3, 2013

(54) METHOD FOR PRIMING A BLOOD LINE SET

(75) Inventors: Wolfgang Biesel, Ottweiler (DE); Maria Millan Galante, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 896 days.

(21) Appl. No.: 12/448,301

(22) PCT Filed: Dec. 19, 2007

(86) PCT No.: PCT/EP2007/011225
§ 371 (c)(1),
(2), (4) Date: Jun. 17, 2009

(87) PCT Pub. No.: WO2008/077573
PCT Pub. Date: Jul. 3, 2008

(65) Prior Publication Data
US 2010/0049115 A1  Feb. 25, 2010

(30) Foreign Application Priority Data
Dec. 22, 2006  (DE) .................. 10 2006 061 184

(51) Int. Cl.
*A61M 37/00* (2006.01)
(52) U.S. Cl.
USPC .......................................... 604/6.11; 604/6.09
(58) Field of Classification Search
USPC ................. 604/4.01–6.16, 408, 411
See application file for complete search history.

(56) References Cited

U.S. PATENT DOCUMENTS

| 4,955,508 | A | 9/1990 | Capanna et al. |
| 5,698,090 | A * | 12/1997 | Bene et al. ................... 210/85 |
| 7,618,584 | B2 | 11/2009 | Lampeter et al. |
| 8,038,639 | B2 * | 10/2011 | Lo et al. ......................... 604/6.1 |
| 2003/0010717 | A1* | 1/2003 | Brugger et al. .............. 210/650 |
| 2004/0222139 | A1* | 11/2004 | Brugger et al. .............. 210/254 |
| 2007/0038191 | A1* | 2/2007 | Burbank et al. ............. 604/317 |
| 2010/0049115 | A1 | 2/2010 | Biesel et al. |

FOREIGN PATENT DOCUMENTS

| DE | 1 225 343 B | 9/1966 |
| DE | 210425 | 6/1984 |
| DE | 85 25 525 | 12/1985 |
| DE | 42 08 054 A1 | 10/1992 |
| DE | 197 04 564 A1 | 8/1998 |
| DE | 100 11 208 C1 | 9/2001 |
| DE | 101 51 343 A1 | 5/2003 |
| DE | 694 34 724 T2 | 5/2007 |
| EP | 0 069 246 A2 | 1/1983 |
| FR | 1 336 893 | 9/1963 |
| FR | 2 593 068 A1 | 7/1987 |
| GB | 2 003 449 A | 3/1979 |

(Continued)

Primary Examiner — Philip R Wiest
(74) Attorney, Agent, or Firm — Jacobson Holman PLLC

(57) ABSTRACT

A method for priming a blood tubing set having a venous line and an arterial line whose connections at the patient side are in communication with two separate inlets of a chamber of, in particular, a bag and whose connections at the machine side are in communication with a dialyzer. The method includes the steps of parallel filling of both the venous and the arterial lines via a feed line so that priming liquid flows through both inlets into the chamber; and circulation of the priming liquid in the circuit of the lines, the dialyzer and the chamber via a pump so that one of the inlets of the chamber acts as an inlet and the other as an outlet.

17 Claims, 3 Drawing Sheets

(56) References Cited

FOREIGN PATENT DOCUMENTS

| JP | 2001-245970 | 9/2001 |
|---|---|---|
| JP | 2006-95184 | 4/2006 |
| WO | WO 94/29440 | 12/1994 |
| WO | WO 03/006139 A1 | 1/2003 |
| WO | WO 2008/077573 A2 | 7/2008 |

* cited by examiner

METHOD FOR PRIMING A BLOOD LINE SET

This is a national stage of PCT/EP07/011,225 filed Dec. 19, 2007 and published in German, which has a priority of German no. 10 2006 061 184.5 filed Dec. 22, 2006, hereby incorporated by reference.

BACKGROUND OF THE INVENTION

1. Field of the Invention

The present invention relates to a method for priming a blood tubing set which comprises a venous and an arterial line.

2. Description of the Related Art

Blood tube sets of this type are used in extracorporeal blood therapies, e.g. in hemodialysis, and form the extracorporeal blood circuit in this process. As a rule, disposable articles are used as the arterial and venous lines which are packed in a sterile manner and have to be filled and flushed prior to the treatment. This filling and flushing of the blood tubing set, called priming, serves the avoidance of a contact of the blood with air in the extracorporeal therapy as well as the cleaning of the blood tubing set and of the dialyzer or dialysis filter. For this purpose, the arterial and the venous lines are filled with a priming liquid, i.e. with a physiological solution, and thus deaerated after they have been connected to the dialyzer at the filter side. After the filling, the ends of the venous and arterial lines at the patient side are usually connected to one another directly or via a connection element so that the priming liquid can circulate in this circuit of arterial line, dialyzer and venous line until the patent is connected to the system. After the connection of the patient, the priming liquid is displaced by the inflowing blood such that a possible contact of the blood with air is reduced to a minimum. In this connection, the volume circulating in blood tubing set is, however, fixedly predetermined by the volume of the blood tubing set so that it can be too small to achieve a sufficient cleaning and deaerating effect depending on the sterilization procedure and/or on the production filter or the production fillers of the filter used. In addition the reconnection of the connections and the application or opening and closing of the valves are prone to operating errors of the dialysis nurse.

A priming method is furthermore known from U.S. Pat. No. 4,955,508 in which a bag with priming liquid and having at least two chambers is used. In this connection, a first chamber is filled with liquid and has two separate inlets which are arranged at the bottom of the bag. The second chamber is empty and only has one inlet. For the filling of the blood tubing set, the arterial line of the blood tubing set is now connected with one of the inlets of the full chamber while the venous line is connected to the inlet of the empty chamber. The liquid from the full chamber thus flows into the blood tubing set and is pumped from there into the empty chamber so that the blood tubing set is filled and flushed. Then the venous line is detached from the inlet of the second chamber and connected to the second inlet of the first chamber, whereupon the priming liquid circulates through the first chamber. If the consumed priming liquid should be replaced by fresh priming liquid before connection to the patient, one of the lines must in turn be removed and be connected to the inlet of a third chamber. A large liquid volume thus admittedly results which can circulate in the blood tubing set and the cleaning effect of the process can thus be increased. However, this is substantially predetermined by the amount present in the bag so that it cannot be adapted to the actually required amount. At the same time, however, a plurality of connection procedures are necessary which can lead to operating errors and additionally include the risk of contamination of the blood tubing set. In addition, mix-ups can occur due to the plurality of different connections on the bag. The transport and other procedures such as the sterilization of the bags are also complicated since the latter are filled with liquid.

SUMMARY OF THE INVENTION

It is therefore the object of the present invention to provide a method for priming a blood tubing set which can be carried out more easily, more reliably and more economically. It is likewise the object of the present invention to provide a corresponding blood tubing set or bag.

In accordance with the invention, this object is solved by a method of priming a blood tubing set having a venous line and an arterial line whose connections at the patient side are in communication with two separate inlets of a chamber, in particular of a bag, and whose connection at the filter side are in communication with a dialyzer, with the method in accordance with the invention comprising the steps: filling the venous line and the arterial line via a feed line, with priming liquid flowing into the chamber via the lines through the inlets; and circulation of the priming liquid in the circuit of the lines, in the dialyzer and in the chamber via a pump so that one of the inlets of the chamber acts as an inlet and the other as an outlet.

The method in accordance with the invention means that it is no longer necessary to make any reconnections between the filling of the blood tubing set and the circulating so that the process for the treating staff is simplified, connecting errors are avoided and the contamination risks associated therewith are omitted. The priming liquid is introduced into the blood tubing set for this purpose via a feed line such that it flows or is pumped into the venous and arterial lines. The feed line is connected for this purpose to a feed line point in either the arterial or the venous line at which the liquid flow can flow from the feed line in both directions through the lines into the chamber. As soon as so much liquid has flown into the chamber that the two separate inlets are in communication with one another by the liquid collected in the chamber, the circulating can begin. For this purpose, the two separate inlets are advantageously arranged at the lower side of the chamber. A bag can e.g. be used in this context at whose lower side the inlets are arranged, while at its upper side a suspension element for the suspending of the bag is arranged.

In comparison with priming methods in which the connections of the venous and arterial lines at the patient side for the circulation of the priming liquid are connected to one another either directly or via an adapter, the filling via the feed line and the circulation via the chamber moreover has the advantage that—where necessary—a substantially larger volume of priming liquid can be circulated. The volume of the priming liquid can thus be kept large or small and thus adapted to the required cleaning effect depending on the sterilization process and/or the production filter or production fillers of the filter used. A substantially better flushing and cleaning of both the blood tubing set and of the dialyzer as well as an improved flushing out of any contaminants thereby results. An improved deaeration also results since a circulation is possible with larger flow rates via the chamber so that microbubbles are mobilized and separated better. Foreign bodies and particles are likewise hereby better removed from the blood tubing set and the dialyzer and are then deposited in the chamber by sedimentation. For this purpose, the inlets of the chamber advantageously extend into it in the manner of a tube so that foreign bodies can be deposited even better. In addition, the recirculation is also possible without any great effort since it is in particular possible to dispense with adapters for this purpose. An extremely simple method thus results in which operating errors are as good as precluded.

After circulation, the consumed priming liquid in the blood tubing set is advantageously replaced by refilling fresh priming liquid from the feed line into the venous line and into the arterial line, with the consumed priming liquid flowing out through the inlets into the chamber. This refilling step is substantially identical to the first filling step. It can thus be ensured before the connection of the blood tubing set to the patient that the priming fluid in the blood tubing set possibly contaminated during the flushing and circulating process is replaced by fresh priming liquid. No reconnection of the connections is required for this purpose either. No additional container for the reception of the consumed priming liquid is necessary either. A simple and reliable method thus results in turn.

The priming liquid is advantageously added via the feed line downstream of a pump in one of the lines on the filling or refilling of the method in accordance with the invention. The liquid flow from the feed line can thus flow in the direction of the chamber from this feed line point due to the pressure from the feed line, while it is pumped to the other inlet of the chamber in the other direction by the pump. Depending on the arrangement of the feed line point and on the running direction of the pump, the priming liquid is pumped either directly into the chamber or first through the dialyzer. In this connection, the feed line point is advantageously located before the pump in the arterial line so that it can run forward and it pumps the liquid out of the feed line into the chamber via the dialyzer, while the liquid flow in the other direction flows directly into the chamber. Alternatively, the liquid can, however, also be added in the arterial line between the pump and the dialyzer, with the pump then, however, having to run backward.

Furthermore, the two inlets of the chamber can advantageously each be opened and closed in the method in accordance with the invention, with clamps advantageously being used. In this connection, the inlets are advantageously closed before the venous and arterial lines are disconnected to avoid a flowing out of the liquid stored in the chamber. In addition, the clamps can regulate the liquid flows through the blood tubing set on the filling or refilling.

Advantageously, in the filling or refilling in accordance with the invention, the portion of the blood tubing set without the pump, in particular the arterial line, is first filled with the pump switched off and the portion with a pump, in particular the venous line, is then filled by operating the pump. A very simple method thus results in which e.g. the arterial line is filled first in that priming liquid runs out of the feed line directly from the feed line point via the arterial line into the bag. If the arterial line is being filled, the venous line can also be filled with priming liquid from the feed line, which flows via the dialyzer and the venous line into the bag, by switching on the pump. This method is in particular of advantage when the priming liquid is supplied from a bag by means of gravity since the flow rates do not have to be controlled for this purpose.

In this connection, a valve which is arranged at the inlet and is connected to the connection of the arterial line at the patient side is advantageously closed to fill the venous line via the pump. There is thus no risk of sucking priming liquid out of the arterial line again via the pump during the filling of the venous line. Only one single valve thus has to be closed for the filling of the blood tubing set, said valve then being opened again for the circulating. However, no further steps of opening and closing of valves is necessary so that a very simple and safe priming method results.

Alternatively, both the arterial line and the venous line can be filled in parallel in that priming liquid runs out of the feed line in the portion without pump and is simultaneously pumped by the pump into the portion with pump. In this connection, the liquid amount conveyed by the pump must naturally be smaller than the liquid amount which flows in from the feed line. The filling of the blood tubing set is thus possible in only one operating step without changes having to be made to the venous or arterial line for this purpose. Operating errors are thus effectively prevented. The switching between filling and circulating is thus also possible in only one operating step in that the inflow from the feed line is switched off. This also increases the safety and the efficiency of the method.

The feed line can advantageously be opened and closed via a valve in the method in accordance with the invention. A clamp which is attached to the feed line can advantageously be used as the valve in this connection. The liquid flow out of the feed line can hereby be set in accordance with the requirements in filling and circulating. The required pressure for the feeding in of the priming liquid from the feed line arises in this connection either due to gravity or due to a feed pump arranged in the feed line. In particular the first filling method, in which first e.g. the arterial line is filled with the blood pump switched off and the venous line is only filled thereafter via the blood pump, is suitable for the filling by means of gravity.

The priming liquid is advantageously pumped through the feed line via a pump in the method in accordance with the invention. The liquid flow flowing in through the feed line can thus be precisely regulated so that in particular the parallel filling of the blood tubing set can be carried out simply by the corresponding setting of the pump rates of the pumps arranged in the feed line and in the extracorporeal blood circuit. In this connection, a larger amount of priming liquid is supplied via the feed line than is e.g. pumped through the venous line so that the remaining liquid flows directly via the arterial line to the bag. The pump can then also replace the valve in the feed line since the feed line can likewise be shut off via the roller pumps usually used.

In addition to the feeding of priming liquid during the filling or refilling of the blood tubing, set, it is also possible to add a specific amount of priming liquid by opening the valve in the feed line or by using the pump during the circulation of the fluid, e.g. in order to replace liquid discharged in the dialyzer. Filter-passing contaminants are separated via the membrane of the filter into the dialysate by this convection. The filter is thereby effectively flushed.

The feed line is advantageously in communication with a second chamber, in particular of a second bag with priming liquid. The priming liquid can thus be added in a simple manner, where the second bag is arranged in an elevated position, in particular when filling via gravity, so that the priming liquid flows into the blood tubing set.

Alternatively, the priming liquid guided into the feed line can also be obtained online from the dialysate. No additional source for the priming liquid is thereby required, which simplifies the method and saves costs since the dialysate and the corresponding apparatus are present anyway. A pump is then advantageously used which pumps the priming liquid through the feed line.

The feed line is advantageously in communication with a substituate port. This is usually provided with a pump so that an exact control of the priming liquid flowing in through the feed line is possible without any additional effort. The substituate port makes physiological liquid available. This physiological liquid can, however, also be used for priming so that apparatus effort can be saved here.

The connection of the arterial line on the patient side is advantageously first disconnected from the inlet of the chamber after the priming in the method in accordance with the invention for the treatment of blood and is connected to the patient; the priming liquid remaining in the blood tubing set is then pumped into the chamber, with blood flowing into the blood tubing set and thereupon the connection of the venous line on the patient side also being connected to the patient. The venous line is thus only connected to the patient when the extracorporeal circuit is completely filled with blood. A minimal number of connection procedures is also only necessary for this purpose so that the method can be carried out simply and reliably. A further container is also not necessary into which the priming liquid would have to be drained off.

Alternatively, after the refilling of fresh priming liquid for the blood treatment, the connections of the arterial line and of the venous line at the patient side can be disconnected from the inlets of the chamber and be connected to the patient, with any priming liquid remaining in the blood tubing set being supplied to the patient at least in part. Clean priming liquid is supplied to the patient in the amount in which blood is removed by this substantially simultaneous connecting of both connections. This is in particular of advantage with patients with unstable circulation since they do not suffer any liquid loss.

A method in accordance with one of the preceding claims, wherein priming liquid is dispensed to the patient during the blood treatment via the feed line, e.g. as a bolus infusion. Since a feed line is anyway present to the blood tubing set for priming liquid, the treatment staff has a the possibility at any time during the blood treatment to supply liquid to the patient e.g. in the event of circulation problems without a new bag with physiological solution e.g. having to be connected for this purpose. Only the corresponding valve has to be opened and closed again in the feed line here or only the corresponding pump has to be actuated.

In the method in accordance with the invention, blood which has remained in the blood tubing set after the removal of the connection of the arterial line at the patient side from the patient is in particular supplied to the patient again via the venous line by addition of priming liquid from the feed line. The total blood taken from the patient can thus also be led back into the patient. It is in addition thus possible to supply liquid to the patient again. For this purpose, liquid removed e.g. during the ultrafiltration in the dialyzer can be replaced at least partly by priming liquid from the feed line without reconnecting have to take place for this purpose. For this purpose, after the blood has been led back to the patient, priming liquid is still conveyed for as long as is necessary to supply the patient with the corresponding amount of physiological solution.

The chamber is advantageously empty at the start of the priming in the method in accordance with the invention. In particular when a bag is used, this has the large advantage that the bag with the chamber for the reception of the priming liquid is initially empty and can thereby be transported and sterilized substantially more easily.

Furthermore, a bag and a blood tubing set are advantageously used which are at least partly pre-connected and are sterilized in their totality. An unnecessary risk for the patient due to later connection procedures is thus avoided.

Furthermore, in the method in accordance with the invention, a bag having only one chamber is advantageously used which then advantageously comprises the two separate inlets at its lower side and a suspension element at its upper side.

There is thus no longer any risk of confusion with respect to the connections since only two connections are present which can be used identically. The physiological liquid required for priming advantageously comes from another bag.

The present invention furthermore advantageously comprises a blood tubing set having a bag with one chamber having two separate inlets and with a venous line and an arterial line which are detachably connectable to the two separate inlets, with a feed line being arranged at one of the lines. The method in accordance with the invention can thereby be carried out using the blood tubing set in accordance with the invention, in which method the priming liquid is added via the feed line and then runs into the bag via the arterial line and the venous line. The feed line is advantageously fixedly connected to the arterial line or to the venous line since the feed line does not have to be disconnected from the blood tubing set. The feed line is advantageously integrated in the arterial line or the venous line at a feed line point, in particular via a T connector. Alternatively, the feed line can also be connectable or connected to the line via a detachable connection. The feed line is furthermore advantageously arranged in the arterial line before a pump segment. The method in accordance with the invention can thereby again be carried out particularly advantageously using this blood tubing set in accordance with the invention.

The present invention furthermore comprises a blood tubing set having a bag with a chamber having two separate inlets and having a venous line and an arterial line which are detachably connectable to the two separate inlets. In this connection, at least one of the lines is pre-connected to the empty bag and packed in a sterile manner with it in accordance with the invention. Unnecessary risks for the patient due to later connection procedures of the bag to this line can thereby be avoided. The use of such a bag having at least one pre-connected line becomes possible by the method in accordance with the invention since in this connection the bag is empty at the start of priming and can thus be sterilized and packed together with the line and also no longer has to be reconnected for the filling and circulating of the priming liquid. To facilitate the insertion of the tubing set into the dialysis machine, only one of the lines is advantageously pre-connected to the bag, with, however, both lines being packed together in a sterile manner together with the bag.

It is obvious to the person of average skill in the art in this connection that the pre-connection of at least one line to the bag independently of the arrangement of the feed line at one of the lines is of great advantage. It is, however, evidently even more advantageous for the blood tubing set in accordance with the invention to have both properties. It is in particular of great advantage for the feed line also to be either pre-connected or fixedly connected to one of the lines and to be packed in a sterile manner together therewith since a further connection procedure can thus be eliminated.

Valves are advantageously arranged at the inlets of the chamber in the blood tubing set in accordance with the invention. They are in turn advantageously made in the form of clamps. The bag can thus be closed simply by the valves so that the venous line and the arterial line can be disconnected from the bag after priming and can be connected to the patient. Equally, the liquid flow through the lines can be set during the filling.

A valve and/or a pump portion is/are furthermore advantageously arranged at the feed line; the valve again advantageously in the form of a clamp. The inflow of the priming liquid can be controlled in this connection. A separate bag with priming liquid or a supply of priming liquid gained online from the dialysate is e.g. advantageously used. The bag with the chamber having the two feed lines, which is used for the circulating and which receives consumed priming liquid, can then be made as a single-chamber bag. This in particular makes it possible that it is empty before the priming so that it can be sterilized and stored easily. In addition, it is thereby possible to use a blood tubing set free of liquid which is pre-connected and sterilized and packed in a sterile manner together, while the priming liquid is supplied via a separate bag or e.g. via the substituate port.

In the priming method in accordance with the invention, only three or four connection procedures are thus necessary for the priming. Only the container with the priming liquid or a port for the provision of the priming liquid thus has to be connected to the feed line and the connections of the arterial line and the venous line at the filter side have to be connected to the dialyzer. Optionally, one of the lines still has to be connected to the not pre-connected inlet of the bag. The total filling and circulating process can then take place without any further reconnecting.

In addition, the method in accordance with the invention using the blood tubing set in accordance with the invention does not require any complicated method steps in which valves have to be opened or closed, or their number is at least reduced. If filling takes place in parallel, only the valve in the feed line has to be opened and closed in the total priming process, while the valves at the inlets of the chamber can remain open the whole time. They only have to be closed when the venous line and the arterial line are disconnected from the chamber and connected to the patient. If a pump is present for the feed line, the total filling and circulating process can also take place completely without the adjustment of valves solely via the control of the pumps. If filling does not take place in parallel, only the valve for the arterial line also has to be closed after the filling and opened before the circulating; however, further steps are not necessary.

The present invention furthermore comprises a method for the provision of one of the blood tube sets described above comprising the steps of: connecting the empty bag to at least one line as well as the common sterilization of the bag and at least one line. The total pre-connected blood tubing set can thus be sterilized in one working step, with a contamination by an only subsequent connection of separately sterilized parts additionally being avoided.

The empty bag and thus the empty blood tubing set of the present invention make it possible in this connection that they can be sterilized in a simple and cost-effective manner using all standard sterilization procedures. The bags filled with solution in accordance with the prior art can, in contrast, not be sterilized using specific standard methods such as ETO sterilization, since with a filled bag obviously no sterilizing fluids can be used for the sterilization.

In the present invention, the common sterilizing of the bag and of at least one line, in contrast, advantageously takes place via a sterilization fluid. These simple and cost-effective sterilization methods can thus be used without problem with the present invention since an empty bag and an empty blood tubing set are used.

The common sterilizing of the bag and of at least one line advantageously takes place using ETO (ethylene oxide). This is a frequently used sterilization gas with which an inexpensive sterilizing method can be realized.

The present invention furthermore comprises a bag for priming a blood tubing set, having a chamber, two separate inlets to the chamber at the lower side of the bag and a suspension element to suspend the bag at an upper side of the bag. The two inlets are arranged on the one side and the suspension element on the other side with respect to a vertical center line of the chamber. In particular the circulating step in accordance with the invention can hereby also be carried out with only a very low amount of priming liquid since the bag comes to be hung obliquely due to the inlets arranged in a corner and to the corner arranged diagonally opposite and the priming liquid thus collects in the corner with the inlets. A particularly favorable flow inside the bag additionally results thereby which supports the air separation and the depositing of particles flushed out. It is possible in this connection by a corresponding filling of the bag to use an amount of priming liquid of any desired size for the circulating so that this amount can be set in dependence on the sterilization method and/or on the production filter or the production fillers of the filter used. A scale applied to the bag can contribute to the simpler operation here.

Inlets and the suspension element advantageously have a spacing from the vertical center line of the chamber which is larger than or equal to one sixth of the width of the chamber. It can be achieved by this arrangement, in which neither the inlets nor the suspension element are arranged in the middle third of the chamber, that the bag hangs ideally obliquely when suspended and the liquid collects above the inlets. Only a little physiological liquid is hereby used to cover the two inwardly lying ends of the inlets. This coverage is, however, necessary due to the avoidance of air circulation.

The bag furthermore advantageously comprises two layers of plastic film welded together, with the suspension element being arranged in an upper corner of the bag and being formed by an obliquely extending weld seam. A stable and secure suspension of the bag can thus be ensured in a simple manner. In this connection, the suspension element can e.g. be a hole in the film forming the bag or a corresponding perforation or round weld seam which still has to be pierced.

Only one chamber is advantageously provided in the bag in accordance with the invention. This single-chamber bag has the advantage that no risk of confusion results with respect to the connections. The physiological liquid required for priming advantageously then comes from another bag. The bag in accordance with the invention can thus also be sterilized and stored better.

The inlets furthermore advantageously project into the chamber in the bag in accordance with the invention in the manner of a tube. This supports the deposition of flushed out particles and foreign bodies in the bag as well as the air separation.

Clamps for the closing of the respective inlet are advantageously arranged at each of the two inlets in the bag in accordance with the invention. The bag can be closed via this clamp prior to the disconnection of the venous line and of the arterial line so that no priming liquid runs out. The use of clamps thus produces a simple and clear handling of the bag.

The inlets furthermore advantageously each have a connection for the connection to a blood tubing set. The two separate inlets can be connected simply and reliably to the connections of the venous line and the arterial line at the patient side via these connections.

A scale is furthermore advantageously applied to the bag in accordance with the invention. It can e.g. be printed on the bag. This scale advantageously shows the liquid level in the bag and thus helps the staff to monitor the individual priming steps.

The bag in accordance with the invention is furthermore advantageously packed in an empty and sterile manner before the priming. Weight advantages in storage and delivery as well as advantages in the sterile use of the bag in accordance with the invention thus result, on the one hand.

As already stated with respect to the blood tubing set, the empty bag of the present invention permits a simple and cost-effective sterilization using all standard sterilization procedures. The bags filled with solution in accordance with the prior art can, in contrast, not be sterilized using specific standard methods such as ETO sterilization, since with a filled bag obviously no sterilizing fluids can be used for the sterilization.

The present invention, in contrast, furthermore comprises a method for the provision of one of the bags described above, with the bag being sterilized using a sterilization fluid, in particular using ETO. These simple and cost-effective sterilization methods can thus be used without problem with the present invention since an empty bag is used.

It is obvious to the skilled person in this connection that it is of great advantage to use the bag in accordance with the invention for the blood tubing set in accordance with the invention or for the method in accordance with the invention. It is equally of great advantage to use the blood tubing set in accordance with the invention for the method in accordance with the invention. In this connection, only individual aspects of the bag in accordance with the invention can be used for the blood tubing set in accordance with the invention, such as the scale in accordance with the invention. This is equally the case with the individual features of the bag and of the blood tubing set which can likewise advantageously be used in the method in accordance with the invention.

BRIEF DESCRIPTION OF THE DRAWINGS

The present invention will now be explained in more detail with reference to an embodiment and to drawings. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
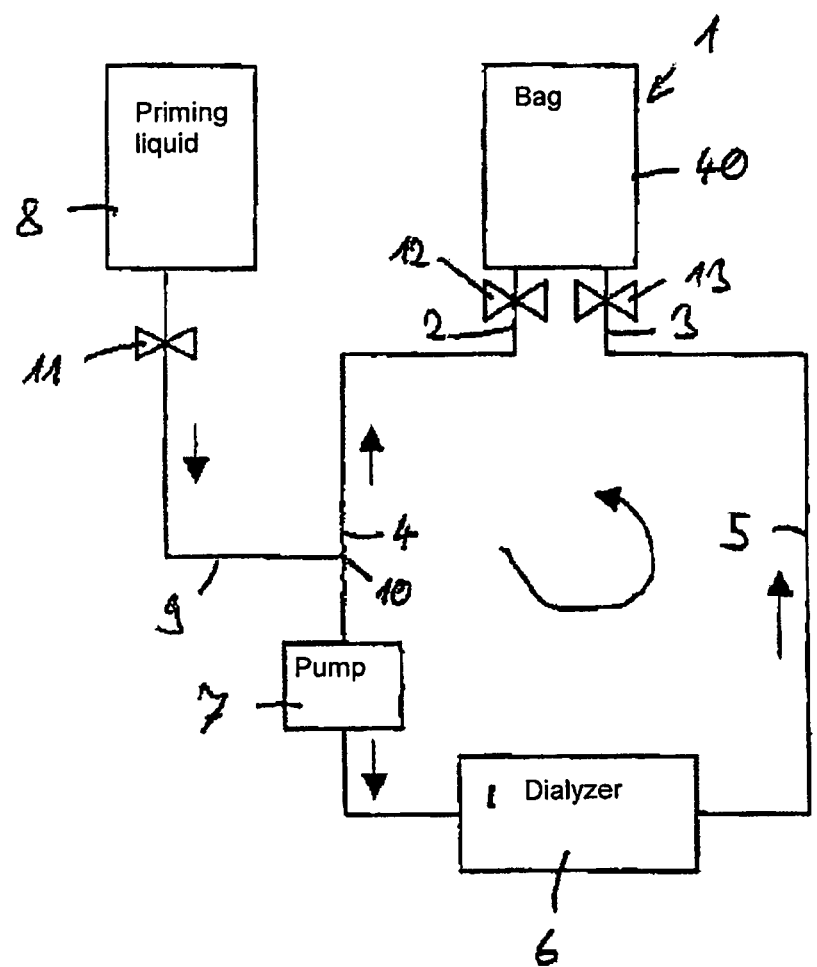
FIG. 1: a schematic diagram of a first embodiment of the method in accordance with the invention using the blood tubing set in accordance with the invention.
Figure 2:
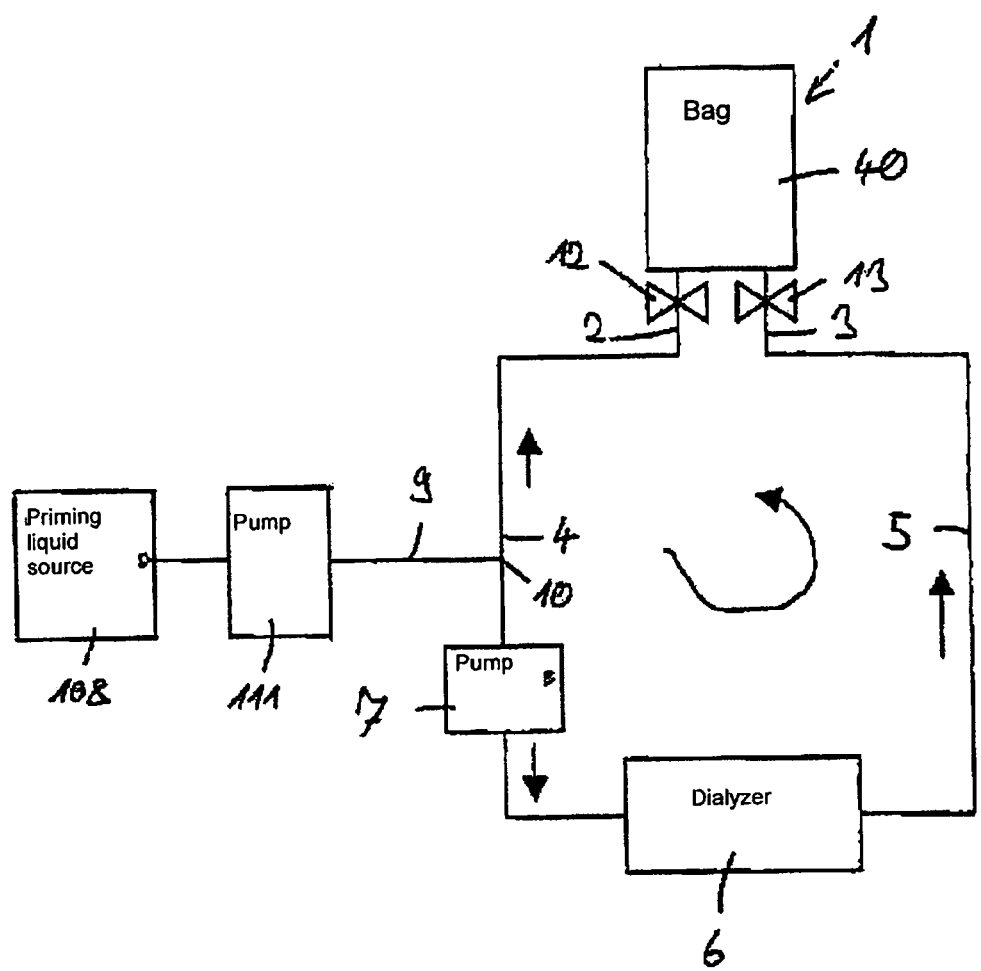
FIG. 2: a schematic diagram of a second embodiment of the method in accordance with the invention using the blood tubing set in accordance with the invention.

FIG. 1 and FIG. 2 show a schematic diagram of a first embodiment and a second embodiment of the method in accordance with the invention for priming a blood tubing set as well as the corresponding blood tubing set in accordance with the invention. The blood tubing set in this connection comprises an arterial line 4 and a venous line 5 which are connected at the patient side to the inlets 2 and 3 of the bag 1. In this connection, the bag 1 is arranged such that the two inlets 2 and 3, which extend separately into the chamber 40 formed by the bag, are arranged at the lower side of the bag. The inlets 2 and 3 can be opened or closed via valves 12 and 13.

The feed line 9 is connected to the arterial line 4 at a feed line point 10, with it being able either to be integrated into the line or be detachably connected thereto. It is a T-connection via which priming liquid can flow into the arterial line 4 via the feed line 9.

The arterial line 4 and the venous line 5 are connected to the blood side of the dialyzer 6 at the filter side. The blood flowing through the blood tubing set during the extracorporeal blood therapy can thus be cleaned and filtered via this dialyzer 6. The pump 7 is arranged between the feed line point 10 of the feed line 9 into the arterial line 4 and the dialyzer 6 so that priming liquid flowing in out of the feed line 9 during the priming can flow directly to the inlet 2 of the bag 1 on the one hand and, on the other hand can be pumped via the pump 7 first to the dialyzer 6 and then via the venous line 5 to the inlet 3 of the bag 1. The pump 7 is advantageously a hose pump which engages at a pump segment in the arterial line 4.

In accordance with the invention, the blood tubing set of feed line 9, arterial line 4, bag 1 and venous line 5 is partly pre-connected and sterilized in common. In this connection, the feed line is already pre-connected to the arterial line and either the arterial line or the venous line is pre-connected to the bag. The pre-connected sterile blood tubing set then packed in a completely sterile manner can thus be used directly with a minimum number of connection procedures, whereby a contamination of the blood tubing set is effectively avoided.

In this connection, a valve 11 is provided at the feed line 9 in the first embodiment shown in FIG. 1 and the feed line can be opened and closed via it. Furthermore, the feed line is connected to a bag 8 with priming liquid. Said bag is arranged in an elevated manner so that the priming liquid flows into the blood tubing set due to gravity after the opening of the valve 11.

In contrast, in the second embodiment shown in FIG. 2, a pump 111 is provided at the feed line 9 and priming liquid is pumped into the blood tubing set through the feed line 9 by said pump. The pump 111 can either engage at a pump segment in the feed line 9 or be connected upstream of the feed line. In this connection, the feed line is connected to a priming liquid source 108 which, as in the first embodiment, can comprise a bag with liquid or a port, e.g. a substituate port, which makes available priming liquid gained online from the dialysate.

Before the priming can start, the bag 8 with the priming liquid or the priming liquid source 108 must be connected to the feed line 9, the arterial line 4 must be inserted into the pump 7 and be connected to the inlet of the dialyzer 6 and the venous line 5 must be connected to the outlet of the dialyzer. The lines must optionally still be inserted into further apparatus not shown here such as air detectors. Furthermore, either the arterial line or the venous line must be connected to the bag since one of the two lines is not pre-connected to facilitate the insertion of the lines into the dialysis machine.

In the first embodiment shown in FIG. 1, the bag 1 is empty at the start of priming, whereas the bag 8 is filled with priming liquid. The valves 12 and 13 of the inlets 2 and 3 of the bag 1 are open for the filling of the blood tubing set so that the air from the blood tubing set can first flow in these. For this purpose, the valve 11 in the feed line 9 is opened so that priming liquid flows out of the bag 8 to the feed line point 10 of the arterial line 4. From there, the priming liquid flows directly to the inlet 2 of the bag 1, on the one hand, due to the pressure in the feed line which is present due to gravity. On the other hand, liquid is also pumped from the feed line 9 by the pump 7 into the dialyzer 6 and through this into the venous line 5, from where the priming liquid flows over the inlet 3 of the bag 1 into it. The priming liquid thus displaces the air in the lines which was present in them. In another respect, other feed line points 10 are also feasible, e.g. between the pump 7 and the dialyzer 6. The pump 7 must then only run backward for the filling of the line. In this connection, in particular the separate filling of the lines is of advantage in which first the arterial line 4 is filled starting from the feed line point 10 with the pump 7 switched off until the priming liquid has displaced the whole air from this portion and flows into the bag 1 via the inlet 2. Then the valve 12 at the inlet 2 is closed, whereupon the pump 7 pumps priming liquid into the rest of the blood tubing set until it is also liberated of air and the priming liquid flows via the inlet 13 into the bag 1. The liquid level in the bag 1 thereupon increases slowly. If the liquid level in the bag has reached a certain minimum level at which the inner ends of the inlets 2 and 3 of the bag 1 are covered by liquid and are in communication via the liquid, the filling can be terminated. However, further priming liquid can still additionally be filled in to increase the liquid amount to be circulated in the next step and to flush the blood tubing set and the dialyzer better. The valve 12 is then opened again for the circulating.

Alternatively, however, both lines can also be filled in parallel in the first embodiment, with an exact setting of the liquid amount pumped by the pump 7 being necessary, however, since it may not exceed the liquid amount flowing in via the feed line due to gravity. The closing and opening of the valve 12 can thus be dispensed with.

If the filling step is ended, the valve 11 in the feed line 9 is closed. The pump 7 now continues to pump liquid through the dialyzer 6 into the venous line 5 and via this via the inlet 3 into the bag 1. The liquid collected in the bag 1 is then sucked in via the inlet 2, which now serves as an outlet, and is so sucked by the pump 7 through the arterial line 4. This circulating step is shown in FIG. 1 as a circular arrow in the centre of the circuit of arterial line 4, dialyzer 6, venous line 5 and bag 1. To flush the filter of the dialyzer 6, a light excess pressure can additionally be applied to the blood side of the filter so that filter-passing contaminants are flushed into the dialysate. The liquid thereby lost can be refilled via the line feed during the circulating.

In the second embodiment shown in FIG. 2, a pump 111 is provided at the feed line 9 which pumps priming liquid from the priming liquid source 108 into the feed line. In this connection, both the separate filling of the arterial line and the venous line described above and the parallel filling is possible. The parallel filling is, however, facilitated here in that the pumping rates of the pumps 111 and 7 can be precisely controlled. Obviously, the pumps 7 and 111 must be set such that the liquid amount pumped by the pump 7 is less than the liquid amount pumped into the feed line 9 by the pump 111. If the pump 111 is the substituate pump of a substituate port, the blood tubing set can be filled in parallel in the second embodiment without additional apparatus effort being necessary.

If the patient should now be connected to the extracorporeal blood circuit, it can be advantageous for the consumed priming liquid which is located in the blood tubing set to be replaced by fresh priming liquid from the bag 8 or from the priming liquid source 108. For this purpose, the same procedure as in the first filling step is carried out in that the valve 11 in the feed line 9 is opened or the pump 111 is actuated. Fresh priming liquid thus in turn flows, on the one hand, via the arterial line 4 backward to the inlet 2 of the bag 1, whereas, in the other direction, the priming liquid fed in via the feed line 9 is pumped by the pump 7 via the dialyzer 6 and the venous line 5 to the inlet 3 of the bag. If the total extracorporeal blood circuit is filled with fresh priming liquid, the valve 11 in the feed line 9 is closed again or the pump 111 is not further actuated.

For the connection of the patient to the extracorporeal blood circuit, the valve 12 of the inlet 2 is now first closed and the connection of the arterial line 4 at the patient side is disconnected from the corresponding connection of the inlet 2. The connection of the arterial line 4 at the patient side is now connected to the patient, whereupon the pump 7 first pumps the remaining priming liquid and then blood via the arterial line 4 through the dialyzer 6 into the venous line 5. The inflowing blood of the patient displaces the priming liquid in the blood tubing set. The connection of the venous line 5 at the patient side can remain connected to the inlet 3 of the bag 1 for so long until the total priming liquid, which was still in the blood tubing set, has flowed into the bag 1. The filling of the blood tubing set with fresh priming liquid can thus also be wholly or partly dispensed with since it anyway flows off into the bag. The valve 13 of the inlet 3 is thereupon closed and the venous line 5 is also disconnected from the inlet 3 and connected to the patient. The actual extracorporeal blood treatment can now start.

Alternatively, since the blood tubing set is anyway filled with clean physiological solution by its refilling with fresh priming liquid, the connecting of the venous line and of the arterial line to the patient can also take place simultaneously so that no liquid is taken from the patient, but the same amount of physiological liquid is supplied to him as blood is taken from him and pumped into the blood tubing set. This can in particular be advantageous with patients with a poor circulation.

The presence of the feed line 9 to the extracorporeal blood circuit also has the advantage during the treatment that liquid can be supplied to the patient at any time e.g. as a bolus infusion in the event of circulation weakness. Additionally, it is possible by the addition of priming liquid, e.g. by hemofiltration in the dialyzer to replace lost liquid at least partly. This usually takes place in that a corresponding amount of priming liquid is supplied from the feed line after the disconnection of the arterial line from the patient.

After the treatment, the connection of the arterial line 4 at the patient side is first disconnected from the patient. To supply the blood still remaining in the blood tubing set back to the patient, priming liquid can now again be given via the feed line 9 into the arterial line 4 which displaces the blood in the blood circuit above the feed line point 10. Only a low amount of blood is thus lost since the connection of the venous line at the patient side is only removed from the patient when the priming liquid from the feed line 9 has completely displaced the blood from the venous line. A certain amount of priming liquid can also still be supplied to the patient to compensate any liquid losses wholly or partly.

A minimum of connecting procedures and switching procedures and only one single bag of priming liquid or one single priming liquid source is thus sufficient during the whole process, which increases the safety, on the one hand, and saves costs, on the other hand. Incorrect operations by the staff are also effectively prevented.

Figure 3:
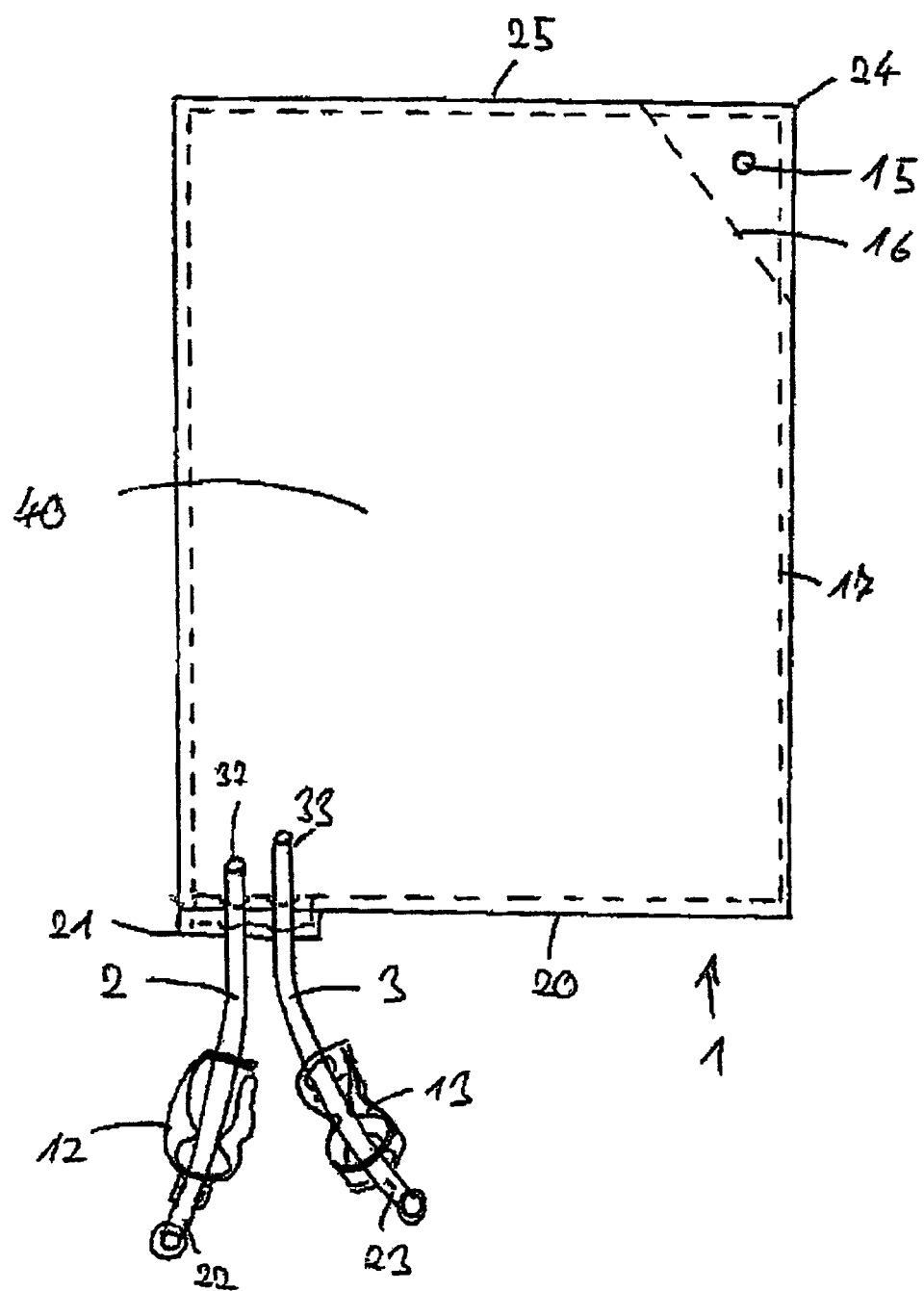
FIG. 3: the bag in accordance with the invention.

FIG. 3 now shows an embodiment of a bag 1 in accordance with the invention which is advantageously used in the method in accordance with the invention or in the blood tubing set in accordance with the invention. The bag 1 comprises two layers of plastic film which are welded together by weld seams 17 in their marginal regions and thus form a single chamber 40. The ends 32 and 33 of the inlets 2 and 3 project into this chamber 40. This in particular has the advantage that foreign bodies and particles collect at the bag's lower side 20 during the circulation in the bag and are no longer flushed into the blood tubing set.

The two inlets 2 and 3 are arranged to the left of a vertical center line of the bag in the embodiment. Contrary to this, the suspension element 15, which is here formed by a simple hole, is arranged to the right of this vertical center line in the upper right hand corner at the upper side 25 of the bag. If the bag 1 is now hung at a hook by means of the suspension element 15, the liquid in the bag automatically flows into the lower left hand corner in which the ends 32 and 33 of the inlets 2 and 3 are arranged. A covering of the two inlets 2 and 3 with liquid can thus also be achieved with a minimum of liquid in the bag, which is indispensable for the circulation of the liquid across the bag. In addition, a favorable liquid flow in the bag results from this oblique arrangement.

The suspension element 15 is arranged in the upper right hand corner 24 of the bag and separated from the chamber 40 of the bag by an oblique weld seam 16. The two inlets 2 and 3 are made in tube shape and have connections 22 and 23 at their ends remote from the bag for connection to the corresponding counter-pieces of the venous line and the arterial line. In addition, clamps 12 and 13 are respectively attached to the inlets 2 and 3 and the liquid flow through the inlets 2 and 3 can be regulated via these.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for priming a blood tubing set having a patient side and a filter side, said blood tubing set including a venous line and an arterial line each having a connection at the patient side and a connection at the filter side, said connections of the venous and arterial lines at the patient side being in communication with two separate ports of a chamber of a bag and said connections of the venous and arterial lines at the filter side being in communication with a dialyzer, said venous and arterial lines, said dialyzer and said chamber forming a circuit, said method comprising the steps of: starting the priming by filling of the venous line and the arterial line with priming fluid via a feed line, said priming liquid from said feed line flowing via the venous and arterial lines through the ports into the chamber, the chamber being empty at the start of the priming; and circulating the priming liquid in the circuit of the venous and arterial lines, the dialyzer and the chamber via a pump so that one of the ports of the chamber acts as an inlet and the other as an outlet.

2. The method in accordance with claim 1, wherein the consumed priming liquid in the blood tubing set is replaced after circulation by refilling fresh priming liquid from the feed line into the venous line and into the arterial line, with the consumed priming liquid flowing through the ports into the chamber.

3. The method in accordance with claim 1, wherein, on filling or refilling, the priming liquid is added downstream of a pump in one of the lines via the feed line.

4. The method in accordance with claim 1, wherein the two ports of the chamber can each be opened and closed via valves.

5. The method in accordance with claim 1, wherein the arterial line is first filled with the pump switched off and the venous line, having the pump thereon, is thereupon filled by operating the pump.

6. The method in accordance with claim 5, wherein a valve which is arranged at the inlet which is connected to the connection of the arterial line at the patient side is closed to fill the venous line via the pump.

7. The method in accordance with claim 1, wherein the feed line has a first end coupled to a priming fluid source and a second end coupled to the circuit, the feed line having a feed line pump located between the priming fluid source and the circuit, both the arterial line and the venous line being filled in parallel as priming liquid runs out of the priming fluid source and into the feed line pump which pumps the priming fluid into the arterial and venous lines.

8. The method in accordance with claim 1, wherein the feed line can be opened or closed via a valve.

9. The method in accordance with claim 1, wherein the priming liquid is pumped through the feed line via a feed line pump located downstream of a priming fluid source.

10. The method in accordance with claim 1, wherein the feed line is in communication with a second chamber of a second bag containing priming liquid.

11. The method in accordance with claim 1, wherein the feed line is in communication with a substituate port.

12. The method in accordance with claim 1, wherein a bag and a blood tubing set are used which are at least partly pre-connected and are sterilized in their totality.

13. The method in accordance with claim 1, wherein said bag has only one chamber.

14. The method in accordance with claim 1, further comprising the steps: connecting the bag with the empty chamber to at least one of said venous and arterial lines; and performing common sterilization of the bag and said at least one line.

15. The method in accordance with claim 14, wherein the common sterilization of the bag and said at least one line takes place via a sterilization fluid.

16. The method in accordance with claim 14, wherein the common sterilization of the bag and at least one line takes place with ethylene oxide (ETO).

17. A method for priming a blood tubing set having a patient side and a filter side and at least one pump, said blood tubing set including a venous line and an arterial line each having a connection at the patient side and a connection at the filter side, said connections of the venous and arterial lines at the patient side being in communication with two separate ports of a chamber of a bag and said connections of the venous and arterial lines at the filter side being in communication with a dialyzer, said venous and arterial lines, said dialyzer and said chamber forming a circuit, said method comprising the steps of: starting the priming by filling the arterial line with priming fluid via a feed line while the pump is turned off, said priming fluid from said arterial line entering the chamber through a first one of said two ports; closing a valve which is arranged at said first one of the ports to fill the venous line by operating the pump, said priming liquid from said venous line entering the chamber through a second one of the said two ports; and circulating the priming liquid in the circuit of the venous and arterial lines, the dialyzer and the chamber via the pump so that one of the two ports of the chamber acts as an inlet and the other as an outlet.

* * * * *